United States Patent
Yamada et al.

(10) Patent No.: US 8,823,941 B2
(45) Date of Patent: Sep. 2, 2014

(54) DETECTION DEVICE

(75) Inventors: Kohei Yamada, Minowa (JP); Nobuaki Hashimoto, Suwa (JP)

(73) Assignee: Seiko Epson Corporation (JP)

( * ) Notice: Subject to any disclaimer, the term of this patent is extended or adjusted under 35 U.S.C. 154(b) by 219 days.

(21) Appl. No.: 13/444,360

(22) Filed: Apr. 11, 2012

(65) Prior Publication Data
US 2012/0262718 A1    Oct. 18, 2012

(30) Foreign Application Priority Data

Apr. 12, 2011  (JP) ................. 2011-087951

(51) Int. Cl.
*G01N 21/00*   (2006.01)
*G01N 21/55*   (2014.01)
*G01N 21/47*   (2006.01)

(52) U.S. Cl.
CPC .............. *G01N 21/553* (2013.01); *G01N 21/55* (2013.01); *G01N 21/554* (2013.01); *G01N 21/474* (2013.01)
USPC ............. 356/436; 356/445; 356/72; 356/301; 356/73

(58) Field of Classification Search
CPC .... G01N 21/553; G01N 21/55; G01N 21/554
USPC ................................. 356/445, 436
See application file for complete search history.

(56) References Cited

U.S. PATENT DOCUMENTS

| | | | |
|---|---|---|---|
| 7,332,327 B2 | 2/2008 | Vikholm et al. | |
| 7,351,588 B2 * | 4/2008 | Poponin | 436/171 |
| 7,510,882 B2 | 3/2009 | Vikholm et al. | |
| 7,869,013 B2 * | 1/2011 | Wang et al. | 356/73 |
| 7,884,930 B2 | 2/2011 | Kirby et al. | |
| 2005/0052813 A1 | 3/2005 | Kobayashi | |
| 2008/0198376 A1 * | 8/2008 | Poponin | 356/301 |
| 2010/0020311 A1 | 1/2010 | Kirby et al. | |
| 2010/0128272 A1 | 5/2010 | Zong et al. | |
| 2012/0105853 A1 * | 5/2012 | Pang et al. | 356/445 |

FOREIGN PATENT DOCUMENTS

| | | |
|---|---|---|
| JP | 2000-356587 | 12/2000 |
| JP | 2005-504294 | 2/2005 |
| JP | 2005-184496 | 7/2005 |
| JP | 3714671 | 9/2005 |
| JP | 2008-513772 | 5/2008 |
| JP | 4203826 | 10/2008 |
| JP | 2009-103651 | 5/2009 |
| JP | 2009-130806 | 6/2009 |
| JP | 2010-511151 | 4/2010 |
| JP | 2011-208985 | 10/2011 |
| WO | WO2004/085976 | 10/2004 |

* cited by examiner

*Primary Examiner* — Tarifur Chowdhury
*Assistant Examiner* — Isiaka Akanbi
(74) *Attorney, Agent, or Firm* — Harness, Dickey & Pierce, P.L.C.

(57) ABSTRACT

A detection device includes a flow channel for a fluid sample, a suction section adapted to draw the fluid sample into the flow channel, an optical device disposed in the flow channel, a light source adapted to irradiate the optical device with light, a light detection section adapted to detect light emitted from the optical device, a microbalance sensor chip having a piezoelectric substrate provided with an oscillation electrode, and disposed in the flow channel, and a quantitative analysis section adapted to perform quantitative analysis on the fluid sample based on output from the light detection section and the microbalance sensor chip. The optical device has a metal nanostructure including projections ranging in size from 1 through 1000 nm, and emits light representing the fluid sample adsorbed to the metal nanostructure.

10 Claims, 14 Drawing Sheets

| SERS INTENSITY VARIATION | QCM VARIATION | QUANTITATIVE OUTPUT PROCESS |
|---|---|---|
| + | + | INCREASE IS DETERMINED, SERS INTENSITY IS OUTPUT |
| + | 0 | REMEASUREMENT IS PERFORMED WITH NO QUANTITATIVE OUTPUT |
| + | - | REMEASUREMENT IS PERFORMED WITH NO QUANTITATIVE OUTPUT |
| - | - | DECREASE IS DETERMINED, SERS INTENSITY IS OUTPUT |
| - | 0 | REMEASUREMENT IS PERFORMED WITH NO QUANTITATIVE OUTPUT |
| - | + | REMEASUREMENT IS PERFORMED WITH NO QUANTITATIVE OUTPUT |

FIG. 4

DETECTION DEVICE

BACKGROUND

1. Technical Field

The present invention relates to a detection device for performing quantitative analysis on an infinitesimal substance on which qualitative analysis is to be performed.

2. Related Art

In recent years, surface enhanced Raman scattering (SERS) spectroscopy using surface plasmon resonance (SPR), and in particular, localized surface plasmon resonance (LSPR), has been attracting attention as a sensitive spectroscopic technique for detecting low-density sample molecules (e.g., see Japanese Patent No. 3714671, JP-A-2000-356587). Surface enhanced Raman scattering denotes a phenomenon that the Raman scattering light is enhanced $10^2$ through $10^{14}$ times on a metal surface having nanometric unevenness. In surface enhanced Raman scattering, the sample molecules are irradiated with an excitation light having a single wavelength such as a laser. The light with a scattering wavelength (the Raman scattering light) shifted from the wavelength of the excitation light by as much as the molecular vibration energy of the sample molecules is spectroscopically detected to thereby obtain the fingerprint spectrum of the sample molecules. As a result, it becomes possible to identify the sample molecules based on the shape of the fingerprint spectrum.

Although surface enhanced Raman scattering can be used for qualitative detection in an infinitesimal concentration of gas molecules due to the electric field enhancement effect of the localized surface plasmon resonance, quantitative analysis has not yet been achieved. One of the causes of this is that the enhanced electric field intensity generated in the localized surface plasmon resonance is exponentially attenuated from the maximum enhanced electric field. According to "Design and Applied Technology of Plasmon Nanomaterial" by CMC Publishing Co., Ltd., p. 181, the SERS intensity "I" caused by the enhanced electric field has been experimentally calculated to have the following relationship with the distance "r" from the enhanced electric field surface.

$$I = \left(1 + \frac{r}{a}\right)^{-10} \quad (1)$$

Here, "a" denotes the radius of a metal nanoparticle. Formula 1 suggests that the SERS intensity varies irrespective of the number of molecules. When the number of surface-adsorbed molecules is large (the coverage is high), it is possible to perform quantitative evaluation based on an ensemble-averaged signal. However, when the coverage is low, an individual molecule provides the intensity expressed by Formula 1, and therefore, the quantitative evaluation is difficult.

JP-A-2009-103651 proposes a SERS quantitative analysis technique wherein molecule samples with a known SERS spectrum are fixed inside a substrate, and quantitative analysis is performed by comparison with the spectrum intensity thereof. However, if the surface coverage of the detection target molecules is low, the number of molecules adsorbed to the enhanced spot decreases, and the effect of Formula 1 becomes conspicuous, and the SERS intensity varies dramatically. Therefore, the proposed method fails to work when the adsorption coverage of the detection target molecules is low (e.g., with an extremely low concentration sample, or a short exposure duration).

JP-T-2008-513772 proposes a quantitative detection device having a combination of attenuated total reflection surface plasmon resonance (SPR) and a quartz crystal microbalance (QCM). Although JP-T-2008-513772 states in paragraphs 0003 and 0005 that the quantitative analysis accuracies of the SPR and the QCM are about 1 ng/cm2, and further states in paragraph 0102 that the two quantitative analysis signals are complementary to each other, there is no specific explanation regarding how the quantitative analysis is performed based on the two signals and, in particular, how the quantitative analysis is performed on an infinitesimal substance. Moreover, since neither the SPR nor the QCM can measure the fingerprint spectrum of the sample molecules of which the quantity is to be determined, it is also technically unachievable to qualitatively detect the sample molecules.

SUMMARY

According to some aspects of the invention, it is possible to provide a detection device for performing quantitative analysis on an infinitesimal substance to be qualitatively analyzed.

An aspect of the invention is directed to a detection device including a flow channel for a fluid sample, a suction section adapted to draw the fluid sample into the flow channel, an optical device disposed in the flow channel, a light source adapted to irradiate the optical device with light, a light detection section adapted to detect light emitted from the optical device, a microbalance sensor chip having a piezoelectric substrate provided with an oscillation electrode, and disposed in the flow channel, and a quantitative analysis section adapted to perform quantitative analysis on the fluid sample based on output from the light detection section and the microbalance sensor chip, wherein the optical device has a metal nanostructure including projections ranging in size from 1 through 1000 nm, and emits light representing the fluid sample adsorbed to the metal nanostructure.

In this aspect of the invention, the light detection section for detecting the light from the optical device is provided with the metal nanostructure having projections in a size range of 1 through 1000 nm, and emits the light representing the fluid sample adsorbed to the metal nanostructure. Therefore, since a fingerprint spectrum unique to the sample is detected, the qualitative analysis of the sample can be performed. Although the spectrum intensity can be the quantitative information of the sample, if the number of sample molecules adsorbed to the metal particles is small, the spectrum intensity fails to be averaged and depends on the parameter "r" in Formula 1, and the spectrum intensity takes various values despite the number of molecules adsorbed to the metal particles is the same. Whether or not the quantitative analysis based on the output intensity of the light detection section is allowed to be performed can be determined based on the increase or decreases in the mass detected by the microbalance chip disposed in combination, and the reliability of the quantitative analysis is enhanced. It should be noted that the optical device and the microbalance sensor chip being "disposed in the flow channel" include configurations wherein either or both are disposed to be engaged to the flow channel so that at least one surface thereof can contact/interact with the sample fluid.

In one aspect of the invention, the optical device and the microbalance sensor chip can be disposed side by side in the flow channel in a plan view, or stacked in the flow channel. The hybrid chip having the optical device and the microbalance sensor chip stacked can be provided with the metal nanostructure of the optical device formed on the oscillation electrode of the microbalance sensor chip. According to this configuration, the number of members of the hybrid chip is reduced, and handling becomes easier because of the single chip.

In one aspect of the invention, a quartz crystal can be used as the piezoelectric substrate of the microbalance sensor chip, and in particular, a surface acoustic wave (SAW) oscillation device can be used as the microbalance sensor chip. The SAW oscillation device can be driven at a GHz order of frequency. Since the sensitivity of the sensor is proportional to the square of the frequency according to the Sauerbrey formula, using the sensor at an increased frequency improves sensitivity.

In one aspect of the invention, if a variation in output intensity of the light detection section and a variation in output of the microbalance sensor chip both increase or decrease, the quantitative analysis section performs the quantitative analysis based on the output intensity of the light detection section. On this occasion, the spectrum intensity of the light detection section has low dependency on the parameter "r" in Formula 1, and can be the quantitative information reflecting the adsorption behavior of the sample molecules.

In one aspect of the invention, if the variation in the output intensity of the light detection section and the variation in the output of the microbalance sensor chip oppositely increase or decrease, or if there is no variation in the output of the microbalance sensor chip, the quantitative analysis section inhibits the quantitative analysis. On this occasion, the spectrum intensity of the light detection section has a high dependency on the parameter "r" in Formula 1, and fails to reflect the adsorption behavior of the sample molecules, and therefore is unreliable for the quantitative information.

BRIEF DESCRIPTION OF THE DRAWINGS

The invention will be described with reference to the accompanying drawings, wherein like numbers reference like elements.

FIG. 4 is a diagram showing an example of a quantitative analysis method of a sample based on the SERS intensity variation and the QCM variation.

DESCRIPTION OF AN EXEMPLARY EMBODIMENT

Hereinafter, a preferred embodiment of the invention will be described in detail. It should be noted that the embodiment explained below does not limit the content of the invention as set forth in the appended claims, and all of the constituents set forth in the present embodiment are not necessarily essential to the invention.

Figure 5:
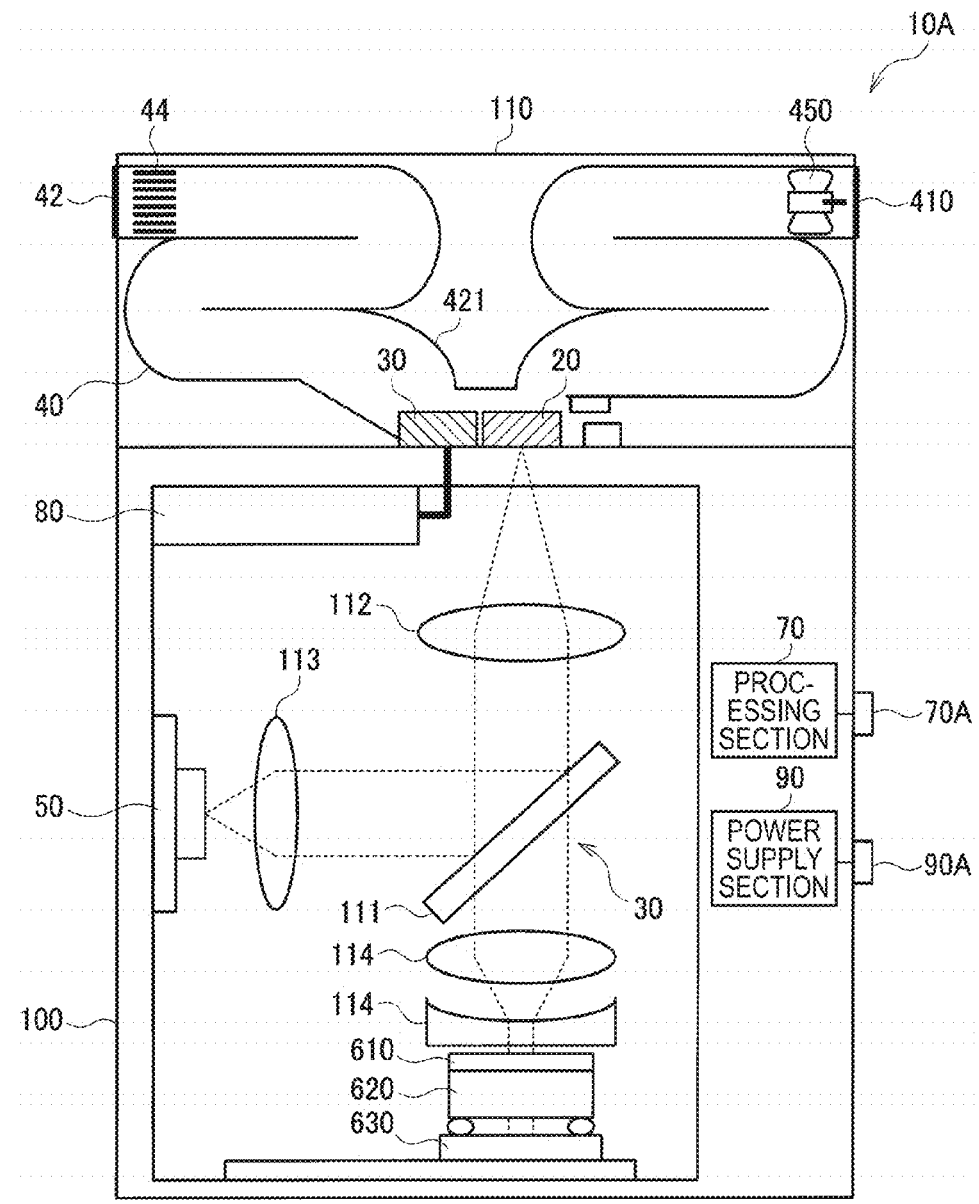
FIG. 5 is a block diagram showing an overall configuration of a detection device having two chips side by side.
Figure 6:
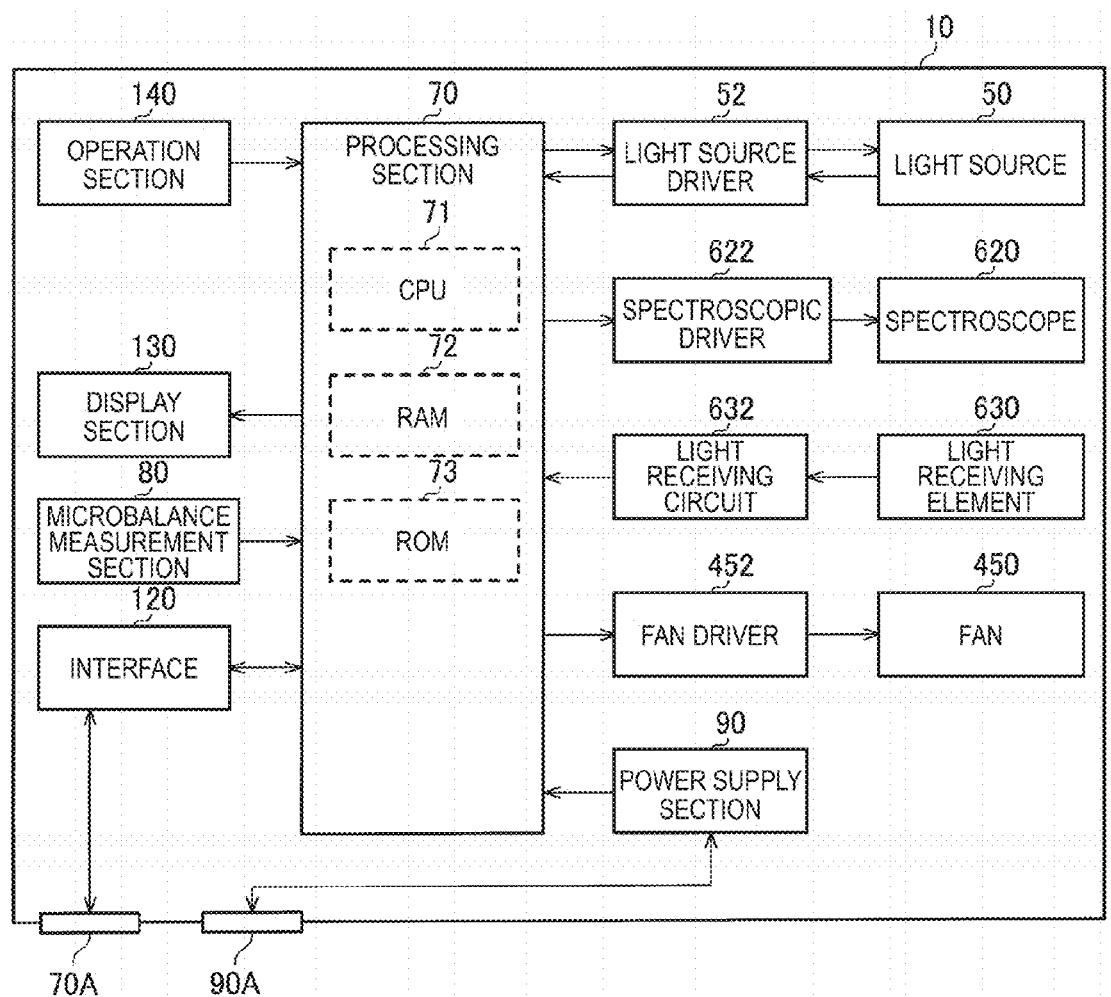
FIG. 6 is a block diagram of a control system of the inspection device.

As shown in FIG. 5 or FIG. 6, the detection device 10A according to the embodiment of the invention is provided with two sensor chips, one is a SERS sensor chip 20 (an optical device), and the other is a microbalance sensor chip 30. These two sensor chips will be explained first.

1. SERS Sensor Chip (Optical Device)

The sensor chip 20 for detecting the Raman scattering light (an optical device for emitting light corresponding to a fluid sample adsorbed thereto in response to irradiation with light) will be explained with reference to FIGS. 1A through 1C. Explanatory diagrams of the principle will also be shown. It should be noted that in the present embodiment, the fluid sample is, for example, air, and the inspection target material can be specific gas molecules (sample molecules) in the air, but is not limited thereto.

Figure 1A:
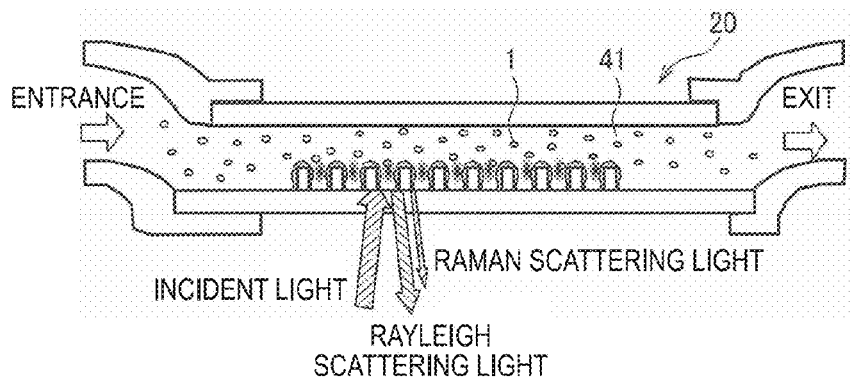
FIG. 1A is an enlarged cross-sectional view of a suction section and an optical device (a sensor chip)

As shown in FIG. 1A, the sample molecules 1 (the inspection target material in the fluid sample adsorbed to the sensor chip 20) are irradiated with incident light (vibration frequency v). In general, most of the incident light is scattered as Rayleigh scattering light, and the vibration frequency v or the wavelength of the Rayleigh scattering light is not varied with respect to the incident light. Part of the incident light, however, is scattered as Raman scattering light, and the vibration frequency (v−v' and v+v') or the wavelength of the Raman scattering light corresponds to the vibration frequency v' (molecular vibration) of the sample molecules 1 in the flow channel 41. In other words, the Raman scattering light is light corresponding to (representing/attributable to) the fluid sample including the sample molecules 1. Although this part of the incident light excites the sample molecules 1 to thereby lose the energy, in some cases, the vibration energy of the sample molecules 1 is added to the vibration energy or the light energy of the Raman scattering light. Such a shift (v') in the vibration frequency is referred to as a Raman shift.

Figure 1B:
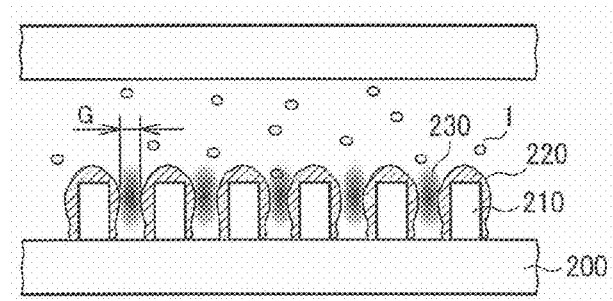
FIGS. 1B and 1C are a cross-sectional view and a plan view showing formation of an enhanced electric field in the optical device.

FIG. 1B is an enlarged view of the sensor chip 20 shown in FIG. 1A. A material that is transparent with respect to the incident light is used for the substrate 200 so that the incident light enters the flat surface of the substrate 200 (see FIG. 1A). As a first structure on the substrate 200, the sensor chip 20 has a plurality of projections 210 made of a dielectric material. In the present embodiment, a resist is formed on the substrate 200 which is made of quartz, crystal, glass such as borosilicate glass, silicon, or the like as the dielectric material transparent with respect to the incident light, and then the resist is patterned using, for example, a deep ultraviolet (DUV) photolithography process. By etching the substrate 200 using the patterned resist, the plurality of projections 210 are arranged, for example, in a two-dimensional array as shown in FIG. 1C. It should be noted that the substrate 200 and the projections 210 can also be made of materials that are different from each other.

As a second structure on the substrate 200, the projections 210 are provided with metal nanoparticles (metal fine particles) 220 made of, for example, Au or Ag and formed by, for example, evaporation or sputtering. It should be noted that the metal fine particles 220 can also be a film made of simple metal or an alloy of any of, for example, Au, Ag, Cu, Al, Pt, Pd, Ni, Mo, and W. As a result, the sensor chip 20 can be provided with a metal nanostructure having projections in a range of 1 through 1000 nm. The metal nanostructure having the projections in a range of 1 through 1000 nm can be formed by a method of fixing the metal fine particles of the above size on the substrate by evaporation, sputtering, and so on, or a method of forming a metal film having an island structure on the substrate besides the method of processing the upper surface of the substrate 200 so as to have the projection structure (with the substrate material) of the above size.

Figure 1C:
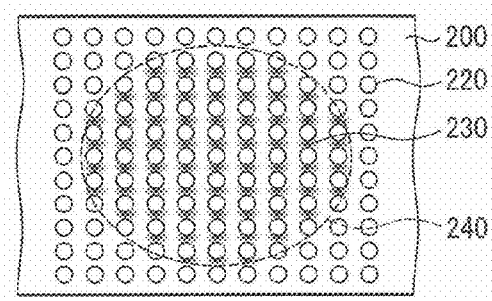

As shown in FIGS. 1B and 1C, in the area 240 where the incident light enters the metal nanoparticles 220 arranged in a two-dimensional pattern, an enhanced electric field 230 is formed in the gap G between adjacent metal nanoparticles 220. In particular, in the case of irradiating the metal nanoparticles 220 that are smaller than the wavelength of the incident light with the incident light, the electric field of the incident light affects the free electrons existing on the surface of the metal nanoparticles 220 to cause resonance. Thus, the electric dipoles due to the free electrons are excited in the metal nanoparticles 220, and the enhanced electric field 230 that is stronger than the electric field of the incident light is formed. This phenomenon is also called localized surface plasmon resonance (LSPR). This phenomenon is unique to the electric conductor having the projections in a range of 1 through 1000 nm which are smaller than the wavelength of the incident light such as metal nanoparticles 220.

In FIGS. 1A through 1C, when irradiating the sensor chip 20 with the incident light, the surface enhanced Raman scattering (SERS) occurs. Specifically, if the sample molecules 1 get into the enhanced electric field 230, the Raman scattering light from the sample molecules 1 is enhanced by the enhanced electric field 230, and the signal intensity of the Raman scattering light increases. In such a surface enhanced Raman scattering, the detection sensitivity can be enhanced even with a minute amount of sample molecules. It should be noted that the metal nanostructure can also be a periodic structure.

Since it is possible to detect only the wavelength attributable to the sample molecules 1 in the Raman scattering light of the fluid sample generated from the SERS sensor chip 20, the SERS signal thus detected corresponds to the fingerprint spectrum of the sample molecules 1.

2. Microbalance Sensor Chip

Figure 2A:
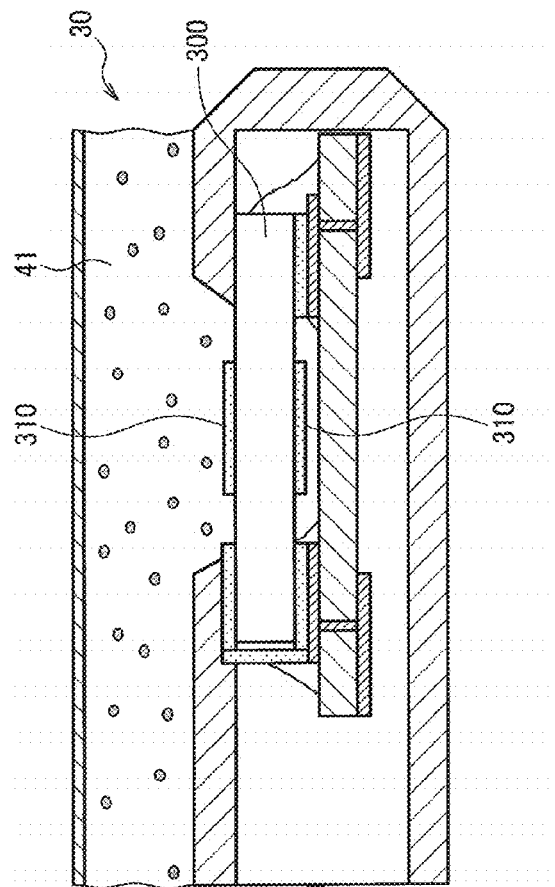
FIGS. 2A and 2B are a cross-sectional view and a plan view of a microbalance sensor chip, respectively.
Figure 2B:
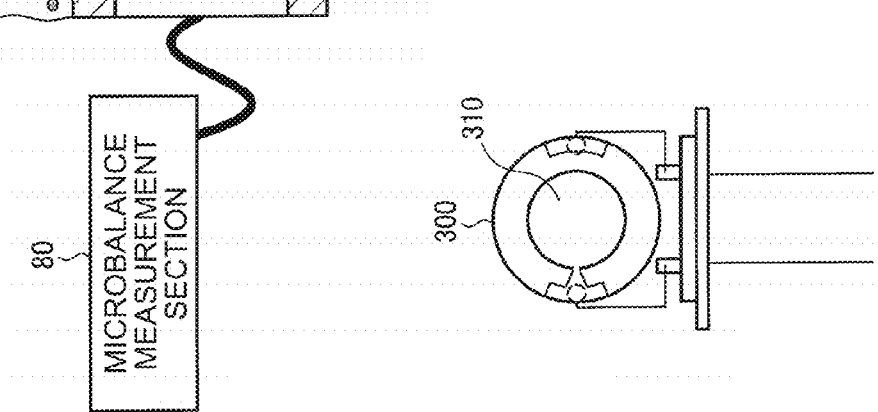

As shown in FIGS. 2A and 2B, the microbalance sensor chip 30 includes a quartz crystal microbalance (QCM) having metal electrodes 310, 310 with an area of, for example, 1 cm$^2$ disposed on two surfaces of a piezoelectric wafer 300 made of quartz. A variation in the piezoelectric wafer 300 can be caused as a mechanical resonance by an alternating electric field due to a reverse voltage effect. The resonant frequency varies in accordance with the mass of the molecules adsorbed to the metal electrode 310. According to the formula of Sauerbrey, assuming that the mass variation is $\Delta m$, the fundamental frequency is F0, the area of the electrode is A, the shearing stress ($2.947 \times 10^{10}$ kg/m·s$^2$) is $\mu q$, and the density of the quartz crystal (2648 kg/m$^3$) is $\rho q$, the frequency variation $\Delta F$ is obtained as follows.

$$\Delta F = -\frac{2F_0^2}{A(\mu_q \rho_q)^{1/2}} \times \Delta m \qquad (2)$$

The resonant frequency decreases as mass increases, and increases as mass decreases. Assuming that the piezoelectric wafer 300 is formed of a quartz crystal AT plate, and the quartz crystal AT plate has a fundamental frequency of 27 MHz, and the vibration variation of 1 Hz is detected, it results that the mass variation of 17.7 ng/cm$^2$ can be detected in the QCM signal according to Formula 2. If the piezoelectric wafer 300 is formed of a quartz crystal surface acoustic wave (SAW) device, and the fundamental frequency is 1 GHz, and the same vibration variation of 1 Hz is detected, the mass variation of 0.44 pg/cm$^2$ can be detected in the QCM signal. As described above, since the sensitivity of the sensor is proportional to the square of the frequency according to the formula of Sauerbrey, it becomes effective to use the sensor at an increased frequency. By using the SAW oscillation device driven with a GHz order of frequency as the microbalance sensor chip 30, a more minute amount of mass variation can be detected. As the SAW oscillation device, those disclosed in JP-A-2009-130806 and JP-A-2005-184496, for example, can be used.

3. Quantitative Analysis Using Two Sensor Chips in Combination

The phenomenon called "adsorption" of the sample molecules 1 described below is a phenomenon in which the number (partial pressure) of colliding molecules, namely the sample molecules 1 colliding with the metal nanoparticles 220, is predominant, and includes one or both of physical adsorption and chemical adsorption. The adsorption energy depends on the kinetic energy of the sample molecules 1, and causes the "adsorption" phenomenon due to the collision if the adsorption energy exceeds a certain value. The adsorption does not require any external force. Further, the suction of the fluid sample to the optical device (the sensor chip) 20 is to cause a suction flow in a flow channel having the optical device (the sensor chip) 20 disposed therein. In other words, to thereby make the fluid sample have contact with the optical device 20.

Figure 3A:
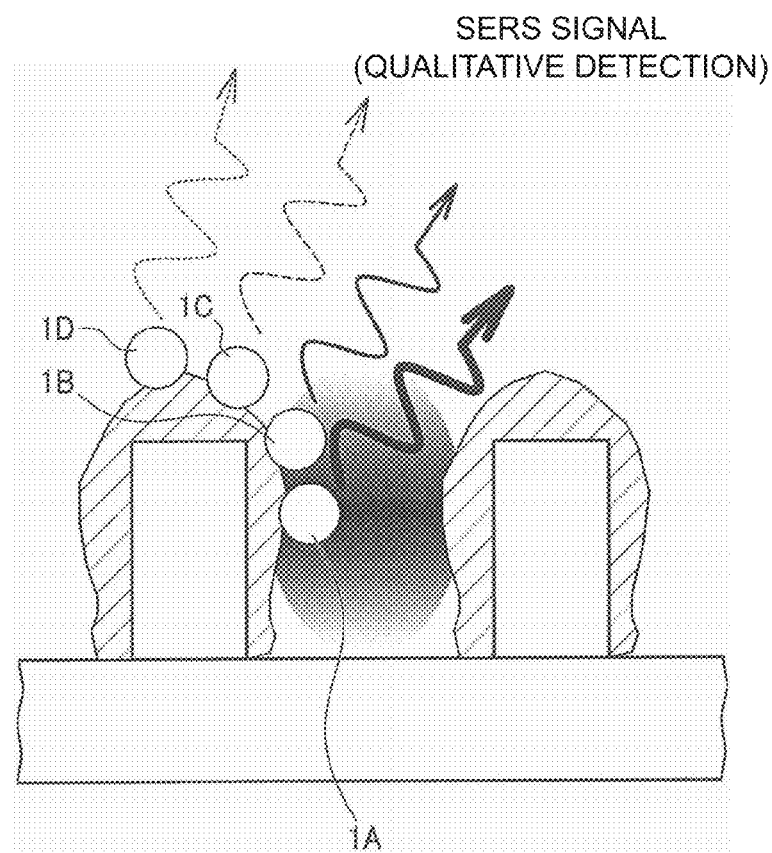
FIGS. 3A and 3B are explanatory diagrams of the SERS intensity dependence on the position of the adsorbed molecules and the QCM signal with no positional dependency.

The sample molecules 1 are adsorbed to the surfaces of the metal fine particles 220 of the SERS sensor chip 20, each of the metal fine particles 220 has a nanostructure, and the sample molecules generate the SERS light, and are detected. FIG. 3A shows the intensity variation in the SERS signal due to the difference in adsorption regions. If the sample molecule 1A is adsorbed between the metal nanostructures, it results that the influence of the localized enhanced electric field is the most significantly exerted (r→0 in Formula 1), and the SERS signal becomes the maximum. As the distance from the enhanced electric field spot increases like the sample molecules 1B, 1C, and 1D, the value of "r" in Formula 1 increases, and therefore, the values of the SERS intensity corresponding to these sample molecules decrease. In the case in which the number of molecules adsorbed to the metal fine particles 220 increases, and the coverage of the metal fine particles 220 is high, since all of the adsorbed molecules can be obtained while averaged in the irradiation spot, the quantitative evaluation of the adsorbed molecules in the SERS sensor chip 20 is highly reliable.

However, in the case in which the number of molecules adsorbed to the metal fine particles 220 is small, and the coverage is low (e.g., having an inferior ppb concentration range, or shortly after the exposure of the sample gas starts), as shown in FIG. 3A, the individual molecule outputs the SERS signal corresponding to its adsorption region, and it results that the non-averaged signals are observed. On this occasion, accurate quantitative determination is not achievable with the SERS sensor chip 20 alone.

Figure 3B:
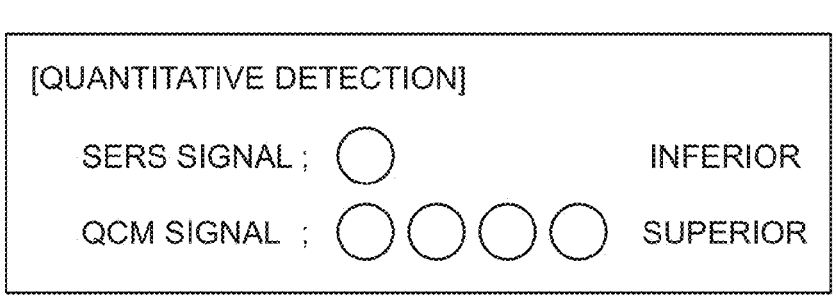

Therefore, in the present embodiment, the output of the microbalance sensor chip 30 is used to determine whether the variation in the SERS intensity is caused by a decrease or an increase in the quantitative determination or the intensity variation of Formula 1 in accordance with the adsorption regions shown in FIG. 3A. In the molecule adsorption condition shown in FIG. 3A, the SERS signal and the QCM signal are as shown in FIG. 3B. As shown in FIG. 3B, the SERS signal is dependent on the intensity values respectively corresponding to the adsorption regions of the four sample molecules 1A through 1D, and therefore, has a value failing to correctly determine the quantity of the four sample molecules 1A through 1D. In contrast, the QCM signal does not correspond to the difference in the adsorption region between the four sample molecules 1A through 1D. It should be noted that since the mass of other molecules not shown in FIG. 3A, namely adsorbed molecules other than the sample molecules 1, is also measured as the QCM signal, it is not possible to measure the mass of the sample molecules 1 adsorbed thereto with only the QCM signal.

As described above, the SERS signal as the fingerprint spectrum can qualitatively evaluate the sample molecules, but is too inferior in reliability to perform quantitative evaluation. The reliability is collateralized by using the QCM signal correctly reflecting the mass variation in combination.

FIG. 4 shows an example of the quantitative determination output processing obtained by the combination of the SERS intensity and the QCM variation. If the SERS intensity varies in a positive direction, it is determined that the number of the adsorbed sample molecules 1 has increased only in the case in which the QCM variation is also positive, and the quantitative evaluation can be performed based on the SERS intensity output. Similarly, if the SERS intensity varies in a negative direction, it is determined that the number of the adsorbed sample molecules 1 has decreased only in the case in which the QCM variation is also negative, and the quantitative evaluation can be performed based on the SERS intensity output.

In combinations other than the two combinations described above, it is determined that the variation in the SERS intensity is the intensity variation of Formula 1 corresponding to the adsorption region as shown in FIG. 3A, and the SERS intensity is not used for the quantitative evaluation. In such cases, re-measurement is performed.

As described above, the quantitative determination display is performed based on the SERS intensity only in the case in which the SERS intensity variation and the QCM variation show the same decreasing or increasing behavior. In contrast, in the case in which the SERS intensity variation and the QCM variation show behaviors that are respectively opposite to each other, and in the case in which the QCM variation is absent, it is determined that the variation is due to the influence of Formula 1, and the re-measurement is performed. The quantitative determination display is inhibited until the SERS intensity variation and the QCM variation show the same decreasing or increasing behavior in the re-measurement.

4. First Configuration Example of Detection Device

As shown in FIG. 5, in the detection device 10A it is possible to dispose the SERS sensor chip 20 and the microbalance sensor chip 30 parallel to each other in the flow channel 421 of the suction section 40 in a plan view. The detection device 10A has a light source 50, a light detection section 60, a processing section 70, a microbalance measurement section 80, and a power supply section 90 besides the two sensor chips 20, 30, and the suction section 4. It is possible to dispose an optical system 110 between the SERS sensor chip 20 and one of the light source 50, the light detection section 60, and both of the light source 50 and the light detection section 60.

The flow channel 421 is formed in the suction section 40 where the sample is drawn in due to the drive of the negative pressure generation section such as a fan 450. The negative pressure generation section is not limited to the fan 450, but can be anything that can generate a negative pressure in the suction section 40 to thereby draw in the fluid sample, such as a pump including a tube pump, a diaphragm pump, and so on. The sensor chip 20 in the flow channel 421 has a structure with the metal fine particles 220 shown in FIG. 1A arranged periodically thereon. The light source 50 irradiates the sensor chip 20 with light via, for example, a half mirror 111 and an objective lens 112 constituting, for example, the optical system 110.

In the sensor chip 20, the localized surface plasmon resonance occurs due to the irradiation with the light from the light source 50, and thus the Raman scattering light emitted from the fluid sample adsorbed to the metal fine particles 220 is enhanced. The detection section 50 detects the Raman scattering light via the half mirror 111 and the objective lens 112.

The microbalance sensor chip 30 is disposed with respect to the flow channel 421 as shown in FIG. 2A (note flow channel 41) to thereby determine the quantity of the molecules adsorbed to the metal electrode 310. The microbalance measurement section 80 is connected to the microbalance sensor chip 30.

The suction section 40 includes the flow channel 421 disposed between a suction port 42 and a discharge port 410. The sample molecules 1 in the fluid sample, namely the target substances, are introduced from the suction port 42 (a carry-in entrance) into the flow channel 421, and are then discharged from the discharge port 410. A dust removal filter 44 can be disposed on the suction port 42 side. The fan 450 is disposed in the vicinity of the discharge port 410, and when operating the fan 450, the pressure (atmospheric pressure) inside the flow channel 421 decreases. Thus, the sample is drawn into the flow channel 421 together with the gas. The sample is discharged via the flow channel 421 around the sensor chips 20, 30. On this occasion, some of the sample molecules 1 are adsorbed to the surface (electric conductor) of the sensor chips 20, 30.

The sample molecules 1 as the inspection target material can be assumed to be rare molecules of, for example, narcotic drugs, alcohol, and residual pesticides, pathogens such as viruses, and so on.

The light source 50 is a laser, for example, and a vertical cavity surface emitting laser can preferably be used therefore from the viewpoint of miniaturization, but the light source 50 is not limited thereto.

The light from the light source 50 is collimated by a collimator lens 113 of the optical system 110. It is also possible to dispose a polarization control element downstream of the collimator lens 113 to thereby convert the light into a linearly polarized light. It should be noted that if the surface emission laser is adopted as the light source 50, and thus linear polarization light can be emitted, the polarization control element can be eliminated.

The light collimated by the collimator lens 113 is guided toward the SERS sensor chip 20 by the half mirror (a dichroic mirror) 111, then converged by the objective lens 112, and then enters the SERS sensor chip 20. The SERS sensor chip 20 is provided with the metal fine particles 220 shown in FIGS. 1A through 1C. The SERS sensor chip 20 radiates, for example, the Rayleigh scattering light and the Raman scattering light due to the surface enhanced Raman scattering. The Rayleigh scattering light and the Raman scattering light from the SERS sensor chip 20 pass through the objective lens 112, and is then guided toward the light detection section (610, 620, and 630 in FIG. 5) by the half mirror 111.

The Rayleigh scattering light and the Raman scattering light from the SERS sensor chip 20 are converged by collecting lenses 114, and are then input to the light detection section. In the light detection section, firstly, the light reaches an optical filter 610. The optical filter 610 (e.g., a notch filter) filters out (i.e., selectively passes) the Raman scattering light. The Raman scattering light is further received by a light receiving element 630 via a spectroscope 620. The spectroscope 620 is formed of, for example, an etalon using the Fabry-Perot resonance, and can be made to have a variable pass frequency band. The wavelength of the light passing through the spectroscope 620 can be controlled (selected) by the processing section 70. The Raman spectrum unique to the sample molecules 1 can be obtained by the light receiving element 630, and the Raman spectrum thus obtained and the data held previously are compared with each other to thereby make it possible to identify the sample molecules 1.

The detection device 10A has a housing 100, and further has the sections 20 through 80 described above in the housing 100, and in addition, can include a power supply section 90, a communication section 70A, and a power supply connection section 90A. The power supply section 90 supplies the light source 50, the light detection section, the processing section 70, the microbalance measurement section 80, the fan 450, and so on with the power from the power supply connection section 90A. The power supply section 90 can be formed of, for example, a secondary battery, and can also be formed of a primary battery, an AC adapter, and so on. The communication connection section 70A is connected to the processing section 70, and transmits data, control signals, and so on to the processing section 70.

In the example shown in FIG. 5, the processing section 70 can send commands to the light detection section, the fan 450, and so on besides the light source 50 shown in FIG. 5, and the processing section 70 is capable of controlling not only the light source 50, but also the light detection section, the fan 450, and so on. Further, the processing section 70 performs the spectroscopic analysis using the Raman spectrum. The processing section 70 can perform the quantitative analysis of the sample molecules according to FIG. 4 based on the SERS intensity from the light detection section and the QCM signal from the measurement section 80. It should be noted that the processing section 70 can transmit the quantitative analysis result, and so on to, for example, external equipment (not shown) connected to the communication connection section 70A.

FIG. 6 is a block diagram of a control system of the detection device 10A shown in FIG. 5. As shown in FIG. 6, the detection device 10A can further include an interface 120, a display section 130, an operation section 140, and so on. Further, as shown in FIG. 6, the processing section 70 shown in FIG. 5 can include a central processing unit (CPU) 71, a random access memory (RAM) 72, a read only memory (ROM) 73, and so on as a control section. Further, the detection section 10A can include, for example, a light source driver 52, a spectroscopic driver 622, a light receiving circuit 632, and a fan driver 452.

Figure 7:
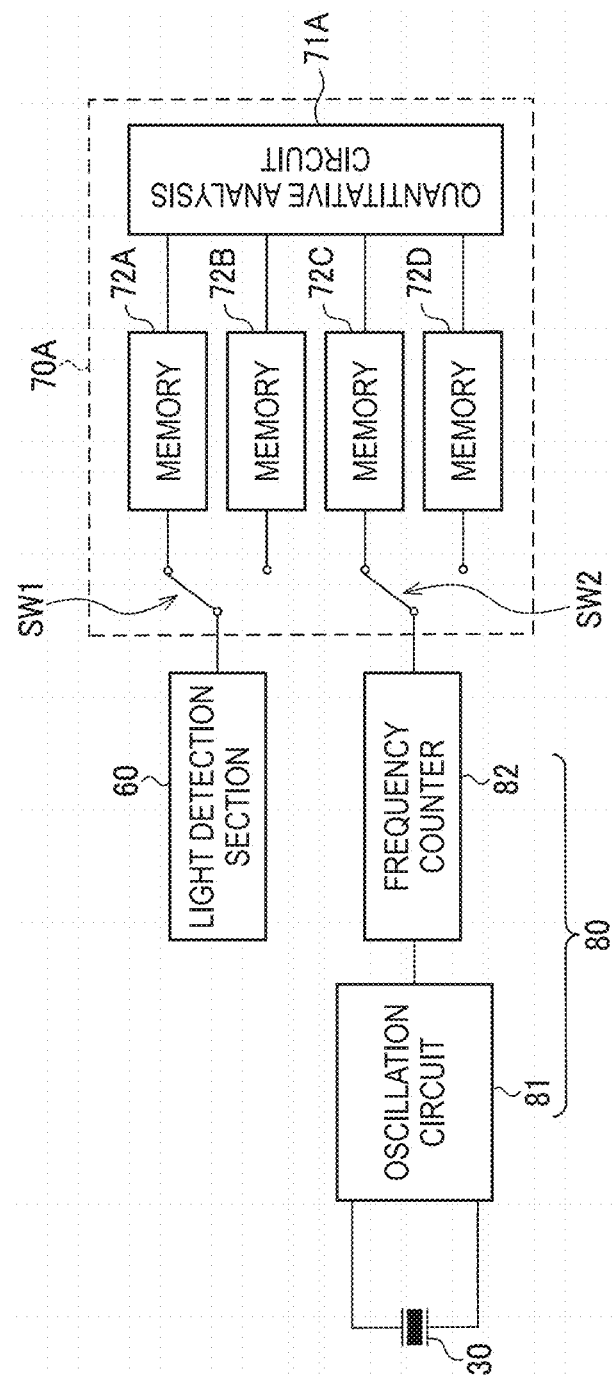
FIG. 7 is a block diagram of a processing system for performing the quantitative analysis.

FIG. 7 shows a circuit block for performing the quantitative analysis. The microbalance measurement section 80 has an oscillation circuit 81 connected to the microbalance sensor chip 30, and a frequency counter 82 for counting the resonant frequency in the microbalance sensor chip 30. The RAM 72 of the processing section 70 has areas shown as memories 72A through 72D, and the CPU 71 of the processing section 70 has a quantitative analysis section 71A.

The SERS signal output in a time-series manner from the light detection section 60 is switched by the switch SW1, and alternately stored to the memories 72A, 72B. The QCM signal output in a time-series manner from the frequency counter 82 is switched by the switch SW2, and stored to the memories 72C, 72D. The quantitative analysis section 71A obtains the SERS intensity variation from the present SERS signal and the previous SERS signal in the memories 72A, 72B. Further, the quantitative analysis section 71A obtains the QCM variation from the present QCM signal and the previous QCM signal in the memories 72C, 72D. Further, the quantitative analysis section 71A can perform the quantitative analysis with the method shown in FIG. 4 based on the SERS intensity variation and the QCM variation thus obtained.

5. Second Configuration Example of Detection Device

Figure 8:
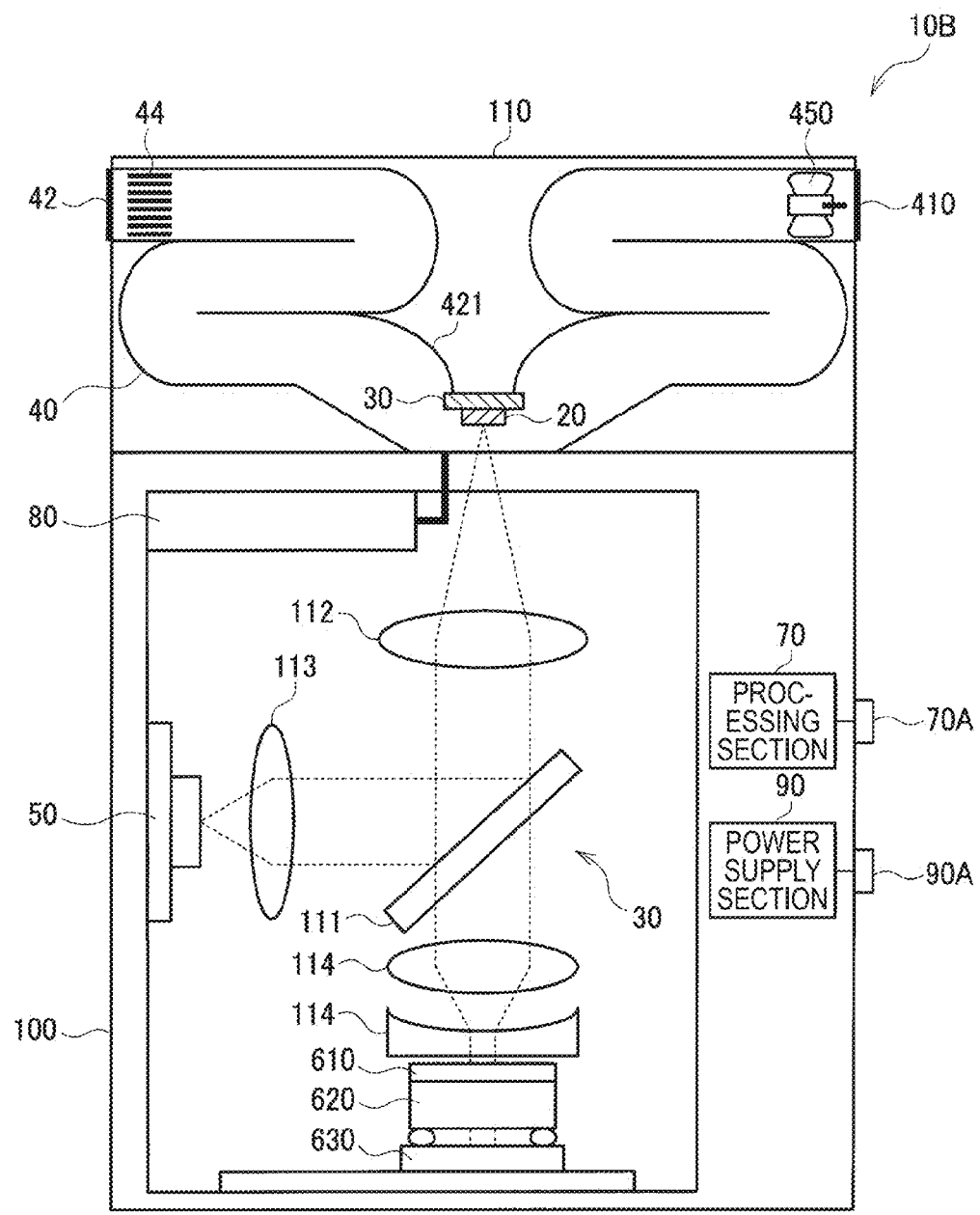
FIG. 8 is a block diagram showing an overall configuration of a detection device having two chips stacked on one another.

FIG. 8 shows another detection device 10B. The point in which the detection device 10B is different from the device shown in FIG. 5 is that the SERS sensor chip 20 and the microbalance sensor chip 30 are stacked on one another. In other words, a hybrid chip obtained by combining the SERS sensor chip 20 and the microbalance sensor chip 30 is used.

Figure 9:
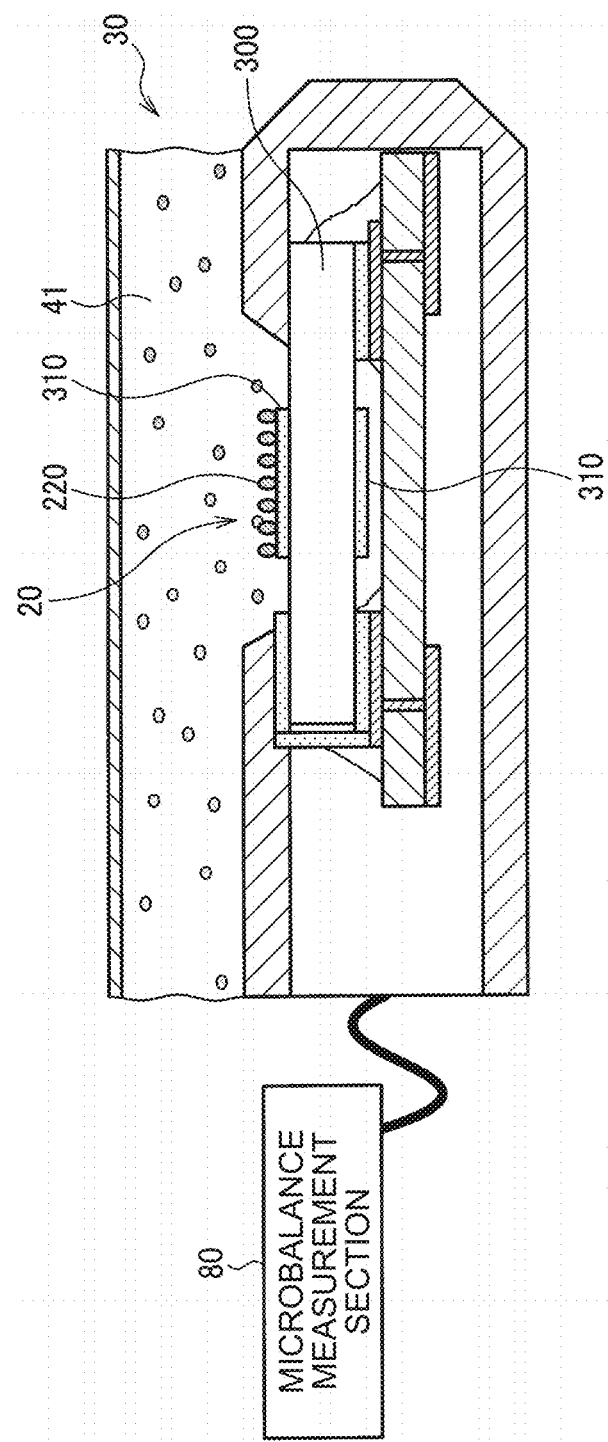
FIG. 9 is a cross-sectional view of a hybrid chip having two chips stacked on one another.
Figure 10A:
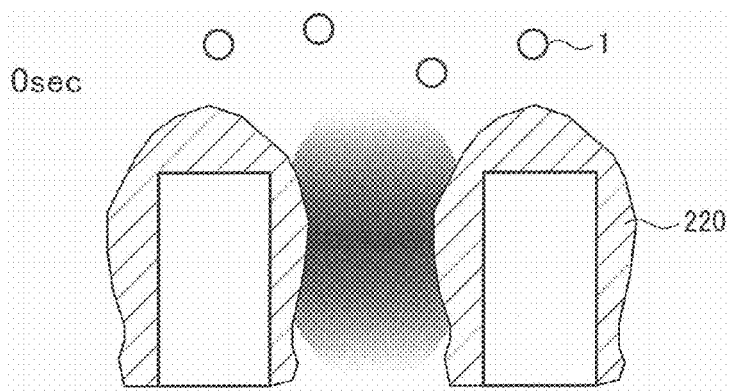
FIGS. 10A through 10D are diagrams showing the behavior of sample molecules.
Figure 10B:
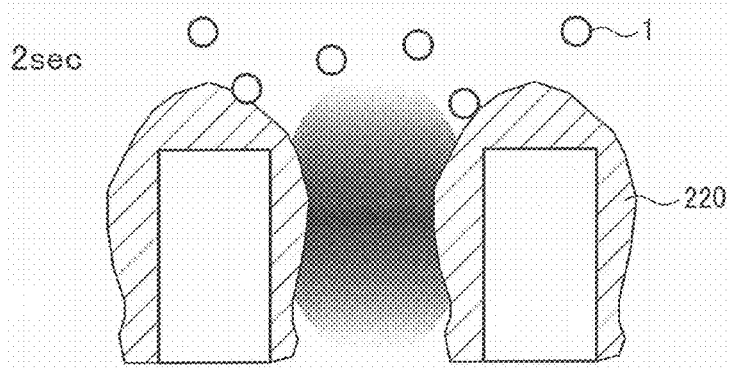
Figure 10C:
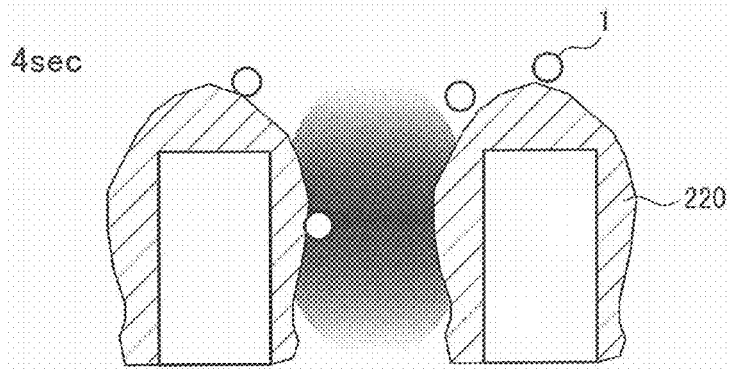
Figure 10D:
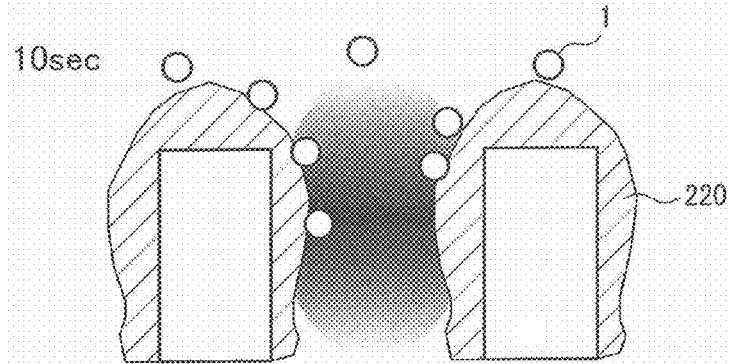

As shown in FIG. 9, the hybrid chip is provided with the metal nanostructure of the metal fine particles 220 formed on one oscillation electrode (the metal electrode) 310 engaged with the flow channel 41 out of the microbalance sensor chip 30 to thereby constitute the SERS sensor chip 20 stacked on the microbalance sensor chip 30. Although it results that the piezoelectric substrate 300 vibrates in a range of MHz through GHz during the detection of the SERS signal, since the exposure time is in a level of millisecond through second, there is no possibility that the vibration of the QCM exerts a harmful influence on the SERS sensor chip 20 as optical noise. Since the hybrid chip has a small number of components, and moreover, is treated as a single chip, reduction in the chip setting operation time can be achieved.

6. Specific Example

Figure 11:
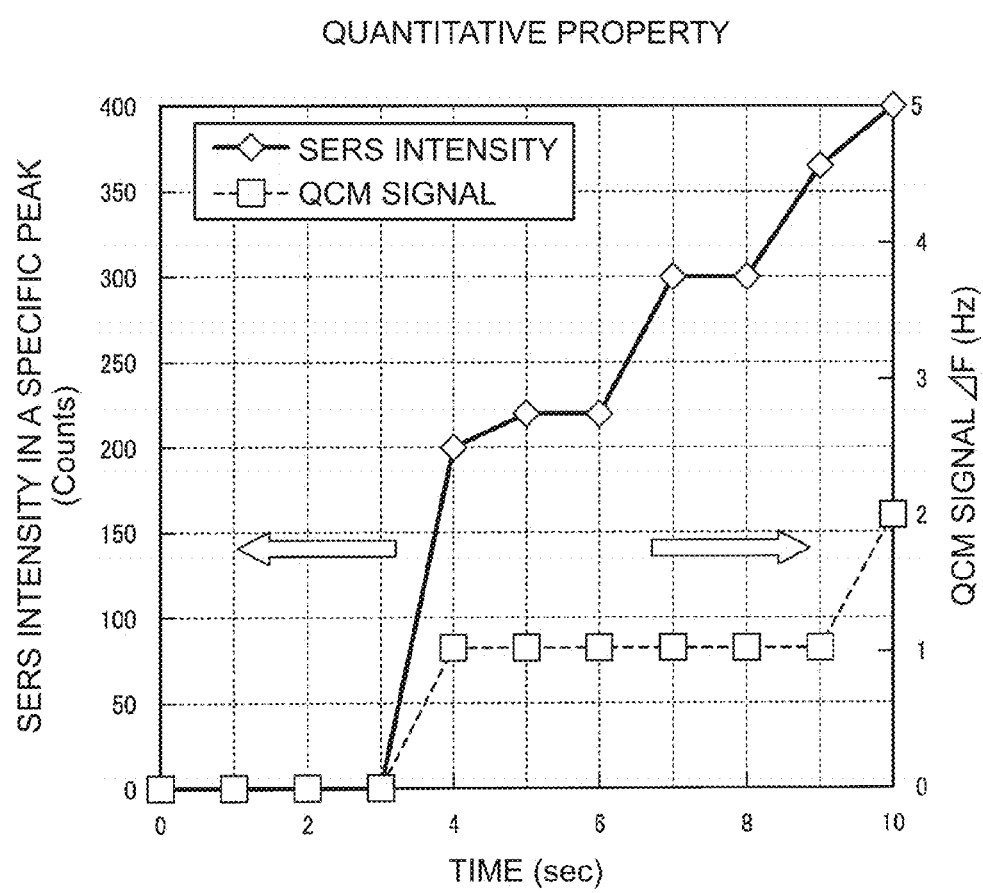
FIG. 11 is a characteristic chart showing the SERS intensity variation and the QCM variation corresponding to FIGS. 10A through 10D.

FIGS. 10A through 10D show the states of the adsorbed molecules at respective elapsed periods of time after making the fluid sample flow through the flow channel 421 of the detection devices 10A, 10B shown respectively in FIGS. 5 and 8 to thereby be exposed to each of the sensor chips 20, 30, and FIG. 11 shows the SERS intensity and the QCM signal thus obtained. The flowing gas in this example is dimethyl sulfide (DMS: $CH_3SCH_3$). Further, FIG. 12 shows the SERS spectrum detected on this occasion.

Figure 12:
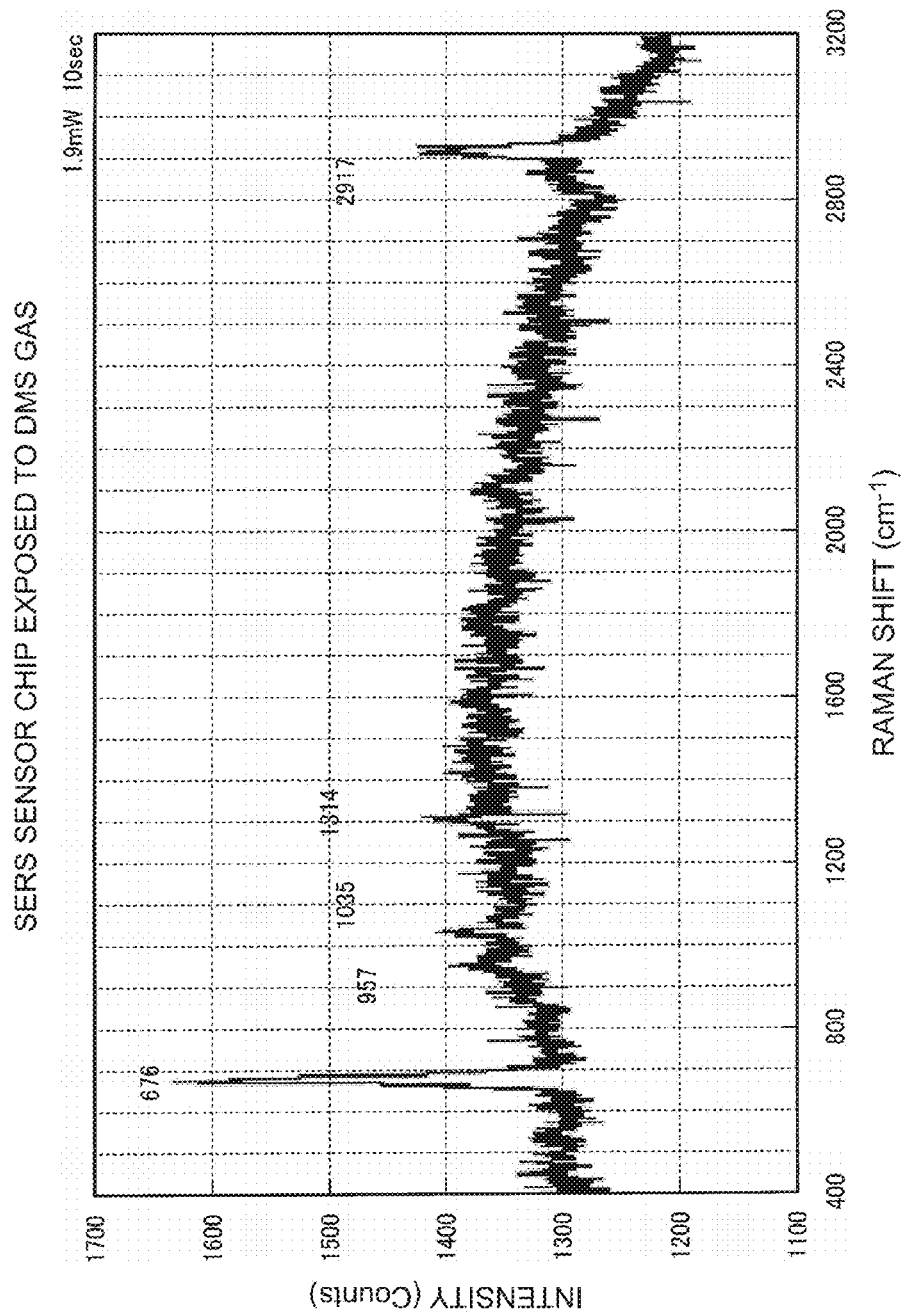
FIG. 12 is a characteristic chart showing the SERS intensity spectrum of the sample molecules.
Figure 13A:
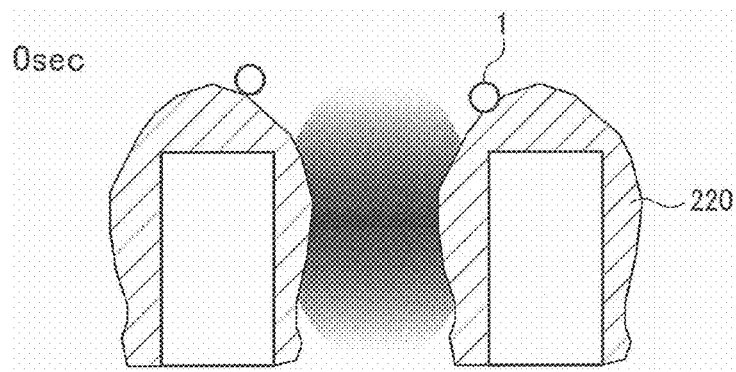
FIGS. 13A through 13D are diagrams showing other behaviors of sample molecules.
Figure 13B:
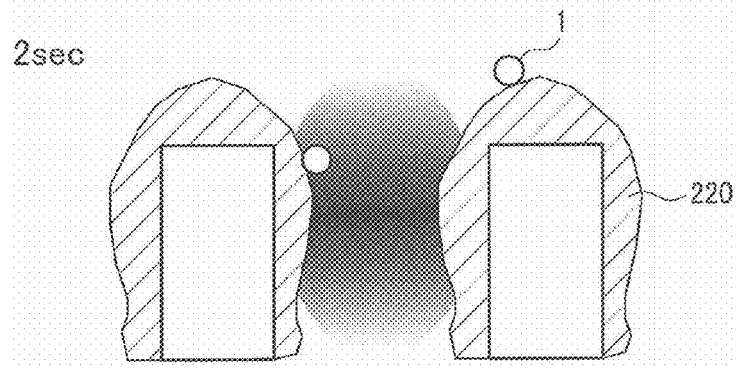
Figure 13C:
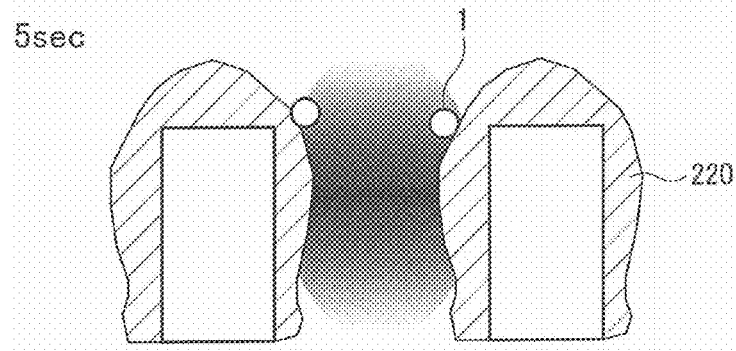
Figure 13D:
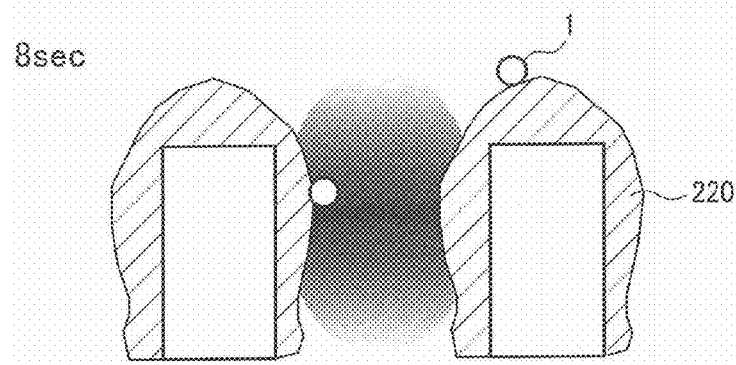

FIG. 12 shows the peaks inherent to the DMS molecules (qualitative detection). The peak at 676 $cm^{-1}$ represents the symmetric stretch vibration of C—S, and provides the highest peak. Focusing on this peak, the SERS intensity values with the respective exposure periods of time are plotted in FIG. 11.

As the microbalance chip 30, a quartz crystal device of 1 GHz having the oscillation electrode (the metal electrode) 310 with an electrode area of 4 $mm^2$ formed on the piezoelectric substrate 300 is used. The frequency variation of 1 Hz shown in FIG. 11 results in the detection of the variation of 0.018 pg in the mass. Converting this into the number of molecules, it is calculated that $1.64 \times 10^8$ DMS molecules are adsorbed to the surface of the oscillation electrode (the metal electrode) 310. On this occasion, it results that 125 molecules exist in the $\phi^2$ μm area of the SERS irradiation spot 240 shown in FIG. 1C.

Incidentally, there is known the fact that a SERS active place (called a hot-site) is located in the gap G (see FIG. 1B) between the metal fine particles 220, and has a size of about 5 nm×20 nm. In the $\phi^2$ μm area of the SERS irradiation spot 240 shown in FIG. 1C, there exist about 280 sites described above. Accordingly, it is calculated that 1 or 2 diffuse molecules come into each of the enhanced electric fields 230 (see FIGS. 1B and 1C) as shown in FIGS. 10A through 10D. With this number of molecules, a non-averaged signal results, and the SERS intensity depending on the parameter "r" of Formula 1 is observed. For example, as shown in FIG. 11, regarding the SERS signal, a roughly proportional number of photons to the exposure time are detected by the light receiving element 630 (see FIG. 5 or FIG. 8). Meanwhile, if the increase in the mass is also recognized in the variation in the QCM as shown in FIG. 11, it is determined that the increase in the SERS is quantitative according to the method shown in FIG. 4. Therefore, the quantitative analysis is performed based on the SERS intensity thus detected.

Figure 14:
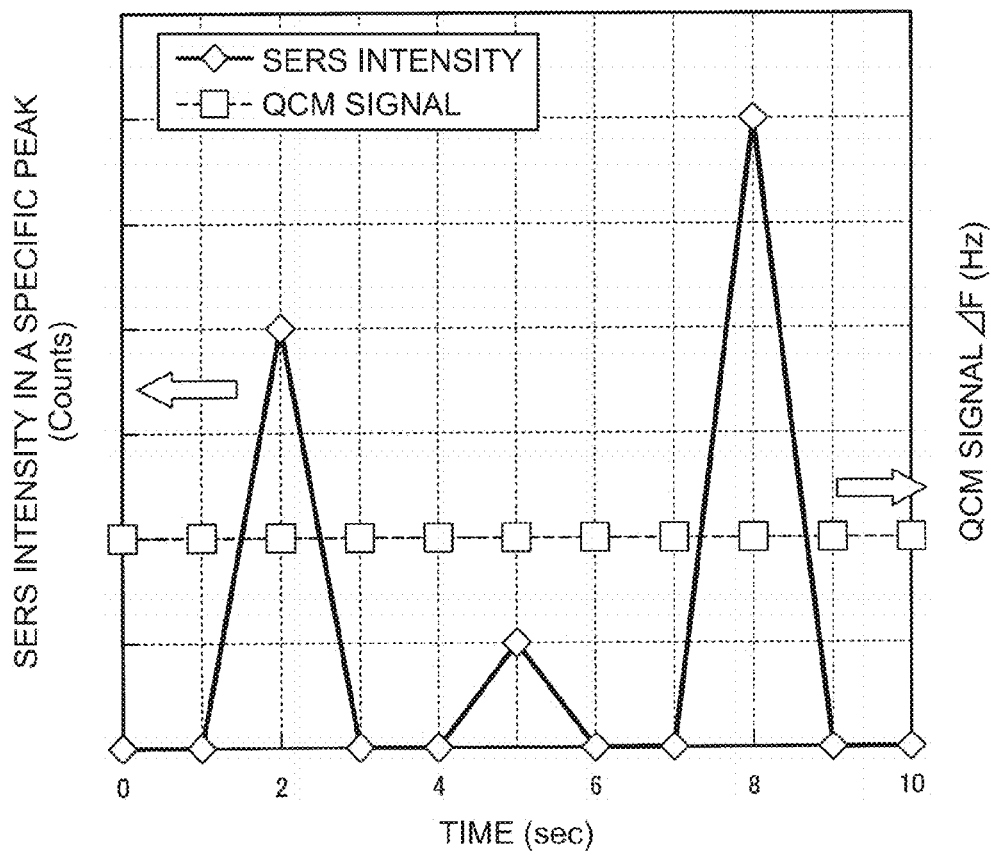
FIG. 14 is a characteristic chart showing the SERS intensity variation and the QCM variation corresponding to FIGS. 13A through 13D.

FIG. 14 shows a measurement result in the case of the behavior of the sample molecules 1 shown in FIGS. 13A through 13D unlike the case of FIGS. 10A through 10D. In the behavior of the sample molecules 1 shown in FIGS. 13A through 13D, although the adsorption positions to the metal fine particles 220 vary, the number of adsorbed molecules does not change.

In this case, although the SERS intensity depending on the parameter "r" of Formula 1 is observed, and the SERS intensity repeats violent fluctuations, the QCM shows no variation. On this occasion, it is determined that the fluctuation of the SERS intensity is caused under the influence of Formula 1 due to the surface diffusion of the adsorbed molecules. As a result, the re-measurement is determined according to the method shown in FIG. 4, and it results that the concurrent measurement of the SERS and the QCM is performed again.

It should be noted that although the present embodiment is hereinabove explained in detail, it can easily be understood by those skilled in the art that various modifications not substantially departing from the novel matters and the effects of the invention are possible.

The entire disclosure of Japanese Patent Application No. 2011-087951 filed Apr. 12, 2011 is expressly incorporated by reference herein.

What is claimed is:

1. A detection device comprising:
    a flow channel;
    a suction section adapted to draw a fluid sample in the flow channel;
    an optical device disposed in the flow channel;
    a light source adapted to irradiate the optical device with light;
    a light detection section adapted to detect light emitted from the optical device;
    a microbalance sensor chip disposed in the flow channel, the microbalance sensor chip having a piezoelectric substrate provided with an oscillation electrode; and
    a quantitative analysis section adapted to perform quantitative analysis on the fluid sample based on output from the light detection section and the microbalance sensor chip,
    wherein the optical device has a metal nanostructure including a projection in a size range of 1 through 1000 nm;
    the optical device emits light representing the fluid sample adsorbed to the metal nanostructure;
    the quantitative analysis section is configured, if a variation in output intensity of the light detection section and a variation in output of the microbalance sensor chip both either increase or decrease, to perform the quantitative analysis based on the output intensity of the light detection section; and
    the quantitative analysis section is configured, if the variation in the output intensity of the light detection section and the variation in the output of the microbalance sensor chip oppositely increase or decrease, or if there is no variation in the output of the microbalance sensor chip, to refrain from performing the quantitative analysis and repeat detecting light emitted from the optical device with the light detection section.

2. The detection device according to claim 1, wherein the optical device and the microbalance sensor chip are disposed side by side in the flow channel in a plan view.

3. The detection device according to claim 1, wherein the optical device and the microbalance sensor chip are disposed in a stack in the flow channel.

4. The detection device according to claim 3, wherein the metal nanostructure is formed on the oscillation electrode of the microbalance sensor chip.

5. The detection device according to claim 1, wherein the piezoelectric substrate is a quartz crystal.

6. The detection device according to claim 1, wherein the microbalance sensor chip is a surface acoustic wave oscillation device.

7. A detection device comprising:
    an optical device;
    a light source selectively irradiating the optical device with light;
    a light detection section periodically detecting light emitted from the optical device;
    a microbalance sensor chip having a piezoelectric substrate including an oscillation electrode; and
    a quantitative analysis section selectively performing quantitative analysis on a fluid sample based on output from the light detection section and the microbalance sensor chip,
    wherein the optical device has a nanostructure of projections;
    the optical device emits light indicative of the fluid sample adsorbed to the nanostructure;
    the quantitative analysis section is configured, if a variation in output intensity of the light detection section and a variation in output of the microbalance sensor chip both either increase or decrease, to perform the quantitative analysis based on the output intensity of the light detection section; and
    the quantitative analysis section is configured, if the variation in the output intensity of the light detection section and the variation in the output of the microbalance sensor chip oppositely increase or decrease, or if there is no variation in the output of the microbalance sensor chip, to refrain from performing the quantitative analysis and repeat detecting light emitted from the optical device with the light detection section.

8. The detection device according to claim 7, wherein the projections have a size range of 1 through 1000 nm.

9. The detection device according to claim 7, wherein the nanostructure is metallic.

10. A method of selectively perming quantitative analysis on a fluid sample comprising:
    providing an optical device having a metal nanostructure of projection;
    providing a microbalance sensor chip having a piezoelectric substrate including an oscillation electrode;

exposing the optical device and the microbalance sensor chip to the fluid sample;
irradiating the optical device with light from a light source so that the optical device emits light representing the fluid sample adsorbed to the metal nanostructure; and
detecting the light emitted from the optical device with a light detector;
wherein:
if a variation in output intensity of the light detector and a variation in output of the microbalance sensor chip both either increase or decrease, performing the quantitative analysis based on the output intensity of the light detection section; and
if the variation in the output intensity of the light detector and the variation in the output of the microbalance sensor chip oppositely increase or decrease, or if there is no variation in the output of the microbalance sensor chip, refraining from performing the quantitative analysis and repeating the detecting step.

* * * * *